(12) United States Patent
Diez

(10) Patent No.: US 7,914,206 B2
(45) Date of Patent: Mar. 29, 2011

(54) X-RAY APPARATUS WITH AN X-RAY SOURCE AND AN X-RAY DETECTOR

(75) Inventor: Michael Diez, Erlangen (DE)

(73) Assignee: Siemens Aktiengesellschart, Munich (DE)

( * ) Notice: Subject to any disclaimer, the term of this patent is extended or adjusted under 35 U.S.C. 154(b) by 955 days.

(21) Appl. No.: 11/803,510

(22) Filed: May 15, 2007

(65) Prior Publication Data

US 2010/0098221 A1    Apr. 22, 2010

(30) Foreign Application Priority Data

May 17, 2006  (DE) .......................... 10 2006 023 211

(51) Int. Cl.
*A61B 6/08* (2006.01)
(52) U.S. Cl. ........................................................ 378/205
(58) Field of Classification Search .............. 378/22–27, 378/205–207
See application file for complete search history.

(56) References Cited

U.S. PATENT DOCUMENTS

| | | | |
|---|---|---|---|
| 4,087,694 A | 5/1978 | Hellstrom et al. | |
| 4,139,776 A * | 2/1979 | Hellstrom | 378/25 |
| 6,501,823 B1 * | 12/2002 | Kim et al. | 378/22 |
| 7,313,219 B2 * | 12/2007 | Endo | 378/22 |
| 2004/0264635 A1 | 12/2004 | Eberhard et al. | |

FOREIGN PATENT DOCUMENTS

DE  10 2004 029 474 A1   1/2005

* cited by examiner

*Primary Examiner* — Irakli Kiknadze

(57) ABSTRACT

The invention relates to an x-ray apparatus with an x-ray source and an x-ray detector, with the x-ray source able to be moved in a first plane and the x-ray detector in a second plane parallel to the first plane and not coinciding with the first plane, with the x-ray source and the x-ray detector always able to be aligned to one another, and a object under examination being able to be arranged between the first plane and the second plane, with, by means of a movement of the x-ray source and a movement of the x-ray detector adapted to the movement of the x-ray source, as well as by means of x-rays leaving the x-ray source, penetrating the object under examination and detected by the x-ray detector, a plurality of two-dimensional projections of the object under examination being able to be recorded in different projection directions relative to the object under examination, from which a spatial presentation of the object under examination is able to be determined.

20 Claims, 2 Drawing Sheets

X-RAY APPARATUS WITH AN X-RAY SOURCE AND AN X-RAY DETECTOR

This application claims priority of German application No. 10 2006 023 211.9 filed May 17, 2006, which is incorporated by reference herein in its entirety.

FIELD OF THE INVENTION

The invention relates to an x-ray apparatus with an x-ray source and an x-ray detector.

BACKGROUND OF THE INVENTION

Despite the ongoing development and new options in the field of radiation-free medical diagnostics, x-ray apparatus remains a mainstay of medical engineering. X-ray recording devices are thus to be encountered in large numbers in medical fields of application. The fields of application extend from x-ray diagnostics, for example the clarification of bone fractures, tumors, cysts, calcifications, trapped air or also preventive examinations, through to fluoroscopic examinations, in angiographies for example, monitoring of medical interventions or localization of medical instruments. In the monitoring of medical interventions in particular and also in the localization of medical instruments a spatial presentation of an object under examination with the medical instrument introduced into it is desirable. This makes it easier for the physician to orient themselves within the object under examination, allows better detection of vessels and organs and enhances the safety of the patient during the intervention.

To determine spatial presentations of an object under examination, regardless of whether these are being used for localization of the medical instrument introduced into the object under examination or to provide imaging support for the diagnosis to be made by the physician, C-arm-x-ray apparatus or computer tomography apparatus is frequently used. With C-arm x-ray apparatus a plurality of two-dimensional projection datasets is recorded from different projection directions relative to the object under examination. This is typically done by means of orbital or angular rotation of the C-arm, to which x-ray source and x-ray detector are attached opposite each other and aligned to each other, around the object under examination. A spatial presentation of the object under examination can be determined from the projection datasets recorded. With computer tomography methods a spatial presentation is produced with the aid of layer imaging methods, by means of spiral computer tomography for example, which uses point-type or line-type projections. The disadvantages of a C-arm x-ray apparatus and also of a computer tomography apparatus are that, at least in one specific time section for recording the projection datasets of the object under examination, a mechanical component of the apparatus—such as a C-arm—is disposed between medical personnel and C-arm. With computer tomography apparatus the patient is surrounded for the entire period of the recording of the projection datasets by a gantry, and is thus only able to be reached by the medical personnel with difficulty.

SUMMARY OF THE INVENTION

The object of the invention is to provide an x-ray apparatus for determining a spatial presentation of an object under examination which requires little space and affords improved access to the object under examination.

The object is achieved by an x-ray apparatus with an x-ray source and an x-ray detector, with the x-ray source able to be moved in a first plane and the x-ray detector in a second plane parallel to the first plane and not coinciding with the first plane, with the x-ray source and the x-ray detector always being oriented opposite one another, and an object under examination being able to be arranged between the first plane and the second plane, with, by means of a movement of the x-ray source and a movement of the x-ray detector adapted to the movement of the x-ray source, as well as by means of x-rays leaving the x-ray source, penetrating the object under examination and detected by the x-ray detector, a plurality of two-dimensional projections of the object under examination being able to be recorded in different projection directions relative to the object under examination, from which a spatial presentation of the object under examination is able to be determined.

This enables a spatial presentation of the object under examination to be determined which demands little space, with there being good access to the object under examination during the examination. The x-ray source and x-ray detector moved during the examination as a rule describes a similar characteristic trajectory, with the characteristic trajectory being passed through with a phase difference of 180 degrees. The form of the trajectory to be described by the x-ray source and the x-ray detector can be designed as required, in particular this can be adapted to an examination environment. In this case x-ray source and x-ray detector are always aligned in relation to each other so that a central x-ray beam emitted by the x-ray source always hits a detector surface presented by the x-ray detector at right angles.

A further advantage of the inventive x-ray apparatus lies in the fact that, by contrast with stationary or mobile C-arm devices, the number of apparatus calibrations is reduced, since x-ray source and x-ray detector are not connected to each other mechanically and thus no strain lag is to be expected from the inherent weight of the device components. Alternatively the inventive x-ray apparatus can also be designed as mobile apparatus. In particular x-ray source and x-ray detector can be supported on a guide device such that these devices are freely movable—within a room, e.g. an operating theater for example.

The plurality of projection datasets can be recorded in stages, in that, during the recording of a projection dataset, the movement of the x-ray source and of the x-ray detector on their trajectories is stopped, and after completion of the recording of the projection dataset, a further movement of x-ray source and x-ray detector into a next trajectory position occurs in order to record a subsequent projection dataset. Alternatively a projection dataset can be recorded while the x-ray source and the x-ray detector are actually moving along their trajectories. The advantage of recording the projection datasets when x-ray source and x-ray detector are at a standstill is that exact position values for x-ray source and x-ray detector for determining the spatial presentations can be determined, which means that the quality of the spatial presentation is generally able to be improved. When on the other hand projection datasets are recorded during the movement of x-ray source and x-ray detector, a positional imprecision of x-ray source and x-ray detector can occur, however the examination time is greatly reduced.

In an advantageous embodiment of the invention the first plane and the second plane are arranged horizontally. This type of arrangement makes it possible to position an object under examination horizontally on a patient support facility, as is conventionally the case. Such an arrangement of x-ray source and x-ray detector allows a further improvement in access to an object under examination.

Furthermore such an arrangement with a horizontal first plane in which the x-ray source moves and a horizontal second plane in which the x-ray detector moves can be used to particular advantage in an operating theater. The horizontal arrangement of the first and second plane, provided they are at a sufficient distance from the object under examination, allows a spatial presentation of the object under examination to be determined by means of an x-ray source without there being a mechanical component of the apparatus between object under examination and medical personnel for a certain section of the time during which the recording is being made. This reduces the effort of determining spatial presentations, e.g. a mobile C-arm-device does not have to be positioned and removed again a number of times, and the intervention time is also reduced. Preferably the distance between the first and second plane and the object is adjustable.

In a further advantageous embodiment of the invention the movement of x-ray source and x-ray detector is embodied as a self-contained movement. This has the advantage of the x-ray source or the x-ray detector being able to be moved for example on a circular path or an elliptical path, which does not require a turning point in the movement of the x-ray source or of the x-ray detector. This allows the tracking speed of the x-ray source or of the x-ray detector on the respective trajectory to be increased, which, with a simultaneously increased rate of recording of projections, permits a reduction in the examination time. Furthermore a small number of acceleration phases along the trajectory means that the friction in the movement of x-ray source or x-ray detector is reduced, by contrast for example with a C-arm with orbital rotation.

In a further advantageous embodiment variant of the invention the movement of x-ray source and x-ray detector features at least one turning point. Since no self-contained trajectory for movement of x-ray source and x-ray detector is selected, a trajectory embodied as a spiral curve for example, turning points during the recording of the plurality of projections can occur during the examination. Since non-self-contained trajectories are selected for the x-ray source and the x-ray detector, a plurality of angles, which are enclosed by a central axis running at right angles to the first and second plane and through the center of the examination area and a central x-ray beam also always running through center of the examination area, can be made possible for the mobile x-ray source and x-ray detector. This enables further projection directions for recording projection datasets to be obtained, which leads to an improvement of a spatial presentation determined.

In a further advantageous embodiment of the invention at least the x-ray source and/or the x-ray detector can be moved in the respective associated plane by at least the x-ray source and/or the x-ray detector being arranged on a movable carrier device. This means that the x-ray source and/or the x-ray detector can be fixed relative to the carrier device, with the carrier device being moved, especially rotated, to record the projection datasets. Since the x-ray source and/or the x-ray detector is rigidly supported relative to the carrier device, and the carrier device is advantageously essentially supported at its mid point, imbalances for the carrier device can be avoided on the one hand. On the other hand wear to the holder or guide of x-ray source and/or x-ray detector can be suppressed through the radial acceleration occurring during the movement, since these units are immobile relative to the carrier device.

Alternatively x-ray source and/or x-ray apparatus can be attached to the carrier device by a releasable attachment facility, so that there is a choice of the way—either rigid or mobile relative to the carrier device—in which the movement of x-ray source and/or x-ray detector is to occur.

In a further advantageous embodiment of the invention the carrier device for the x-ray source and/or the x-ray detector can be adjusted in its position and/or orientation relative to the object under examination. This means that the angle, which the central axis running through the center of the examination area, which is at right angles to the first and second plane, makes with the center x-ray beam which also runs through the center of the examination area is enlarged or reduced, which again influences the spatial presentation that can be determined.

With x-ray sources with small spatial dimensions it is especially possible to record the projection datasets in a position very close to the object under examination. The direct proximity to the object under examination means that the intensity of the x-ray source can also be reduced, which reduces the x-ray dose for the object under examination. This embodiment of the examination is particularly worthwhile if small, delimited areas of the object under examination are to be examined.

Adjustment means can be provided for adjusting the position and/or orientation of the carrier device on which the x-ray source and the x-ray detector are arranged. The adjustment of the position and/or orientation of the carrier device allow the orientation of the first or the second plane to be adjusted, i.e. the horizontal arrangement of first and second plane to be changed to a vertical arrangement of the first and second plane for example. Likewise any orientations of the first and second plane between horizontal and vertical orientation are possible. In such cases the object under examination continues to be always able to be arranged between the first and the second plane. This provides a plurality of options for implementing recording of a plurality of projection datasets using the inventive apparatus.

BRIEF DESCRIPTION OF THE DRAWINGS

Further advantages of the invention emerge from an exemplary embodiment which is described in greater detail with reference to the subsequent drawings, in which.

The figures are depicted as schematic diagrams.

DETAILED DESCRIPTION OF THE INVENTION

Figure 1:
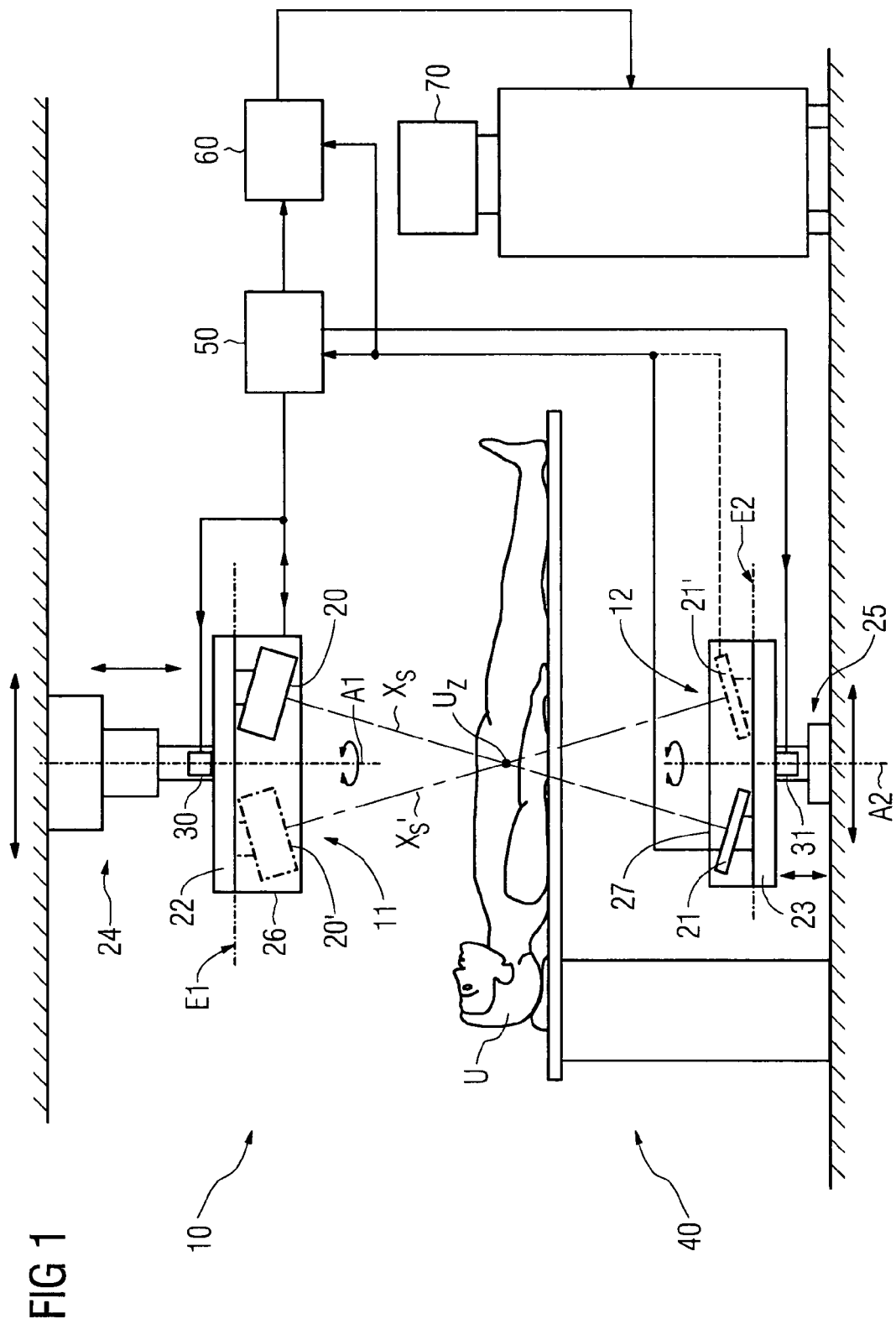
FIG. 1 is a side view of an inventive x-ray apparatus at a medical workstation.

FIG. 1 shows an inventive x-ray apparatus 10 at a medical workstation. The x-ray apparatus 10 features an x-ray source 20 which is fixed to a carrier device 22 that can be rotated around a central axis A1, referred to below as the x-ray source carrier device. The x-ray source carrier device 22 can be any shape, for example in the shape of a circular plate, rectangular plate or also an outrigger or a support arm. In FIG. 1 the x-ray carrier device 22 is embodied as a circular plate.

The x-ray source carrier device 22 is supported on an x-ray source holder device 24. The x-ray source holder device 24 is embodied in the exemplary embodiment as an extendable telescopic arm which can be moved by means of a ceiling-mounted guide apparatus not shown. The x-ray source carrier device 22 is advantageously supported relative to the x-ray source holder device 24 to allow rotation around the central axis A1—useful for the exemplary embodiment. In the exemplary embodiment the x-ray source 20 is attached to allow it to be released from the associated carrier device 22.

Alternatively an x-ray source carrier device not able to be rotated in relation to the central axis A1 can be provided, with however the x-ray source 20 able to be moved relative to the x-ray source carrier device 22, preferably by a motor, in a trajectory predetermined by guide means. The x-ray source carrier device 22 is however preferably able to be rotated relative to the x-ray source holder device 24 around at least one other pivot axis, for example an axis running at right angles to the recording plane through the attachment point of x-ray source carrier device 22 and x-ray source holder device 24.

By rotating the x-ray source carrier device 22 around the central axis A1, with the x-ray source 20 being fixed relative to the x-ray source carrier device, the x-ray detector describes an even, circular trajectory. A plane assigned to the movement of the x-ray source 20 on the trajectory in FIG. 1 is designated as the first plane E1.

Furthermore the x-ray apparatus 10 features an x-ray detector 21, on which a carrier device 23 assigned to the x-ray detector 21, referred to below as the x-ray detector carrier device, is arranged. The x-ray detector carrier device 23 is supported on an x-ray detector holder device 25 rotatable around a central axis A2. The central axis A2, around which the x-ray detector carrier device 23 can be rotated, coincides in the exemplary embodiment with the central axis A1, around which the x-ray source carrier device 22 can be rotated. The x-ray detector holder device 25 assigned to the x-ray detector carrier device 23 is height-adjustable and able to be moved by means of a floor-mounted guide device. The x-ray detector 21 is—like the x-ray source 20 —also rigidly attached in a releasable manner to the x-ray detector carrier device 23 assigned to it. A plane assigned to the movement of the x-ray detector 21 on the circular trajectory in FIG. 1 is referred to as the second plane E2.

As an alternative to an x-ray detector 21 arranged rigidly relative to the x-ray detector carrier device 23, an x-ray detector 21 able to be moved relative to the x-ray detector carrier device 23 can be provided, with the x-ray detector 21 preferably being able to be moved by a motor relative to the x-ray detector carrier device 23 in a trajectory predetermined by guide means.

The movements of x-ray source 20 and x-ray detector 21, regardless of whether this occurs by means of a relative movement of x-ray source 20 and x-ray detector 21 to the respective carrier device 22 or 23, or whether the respective carrier device 22 or 23 along with x-ray source 20 or x-ray detector 21 are in this case always adapted to one another so that an x-ray center beam $X_s$ leaving the x-ray source 20 always hits the x-ray detector 21 during the examination essentially in the center point of a detector surface presented by the x-ray detector 21.

The carrier device 22 and the x-ray source 20 will be referred to below as the x-ray source device. The x-ray source device is covered by a housing 26 which features an x-ray exit area not shown in FIG. 1 from which x-ray beams can exit. The x-ray beam exit area can for example be embodied as a housing opening or as a window transparent to x-rays. The housing 26 of the x-ray source device can be rotated along with the x-ray been device itself while an examination of the object under examination U is being conducted. Advantageously however the housing 26 remains at rest during the recording of projection datasets and only the x-ray source carrier device 22 moves, along with the x-ray source 20.

The x-ray detector 21 and the x-ray detector carrier device 23, referred to below as the x-ray detector device, are also, in a similar way to the x-ray source device, covered by housing 27 which is essentially transparent to x-rays in at least some areas, to prevent access to moving parts, and thus to avoid danger to the patient and/or of the medical personnel. The housing 27 is in such cases advantageously designed so that there is no effect or at most a negligible effect of the x-ray beams penetrating the object under examination U on the quality of the spatial presentation of the object under examination U to be determined. The housing 26 for the x-ray source device or the housing 27 for the x-ray detector device are not absolutely vitally necessary for implementing the invention.

To rotate the x-ray source carrier device 22 along with the x-ray source 20 around the central axis A1 and to rotate the x-ray detector carrier device 23 of the x-ray detector 20 around the central axis A2, the x-ray source carrier device 22 of the x-ray source is assigned an x-ray source drive device 30. The x-ray detector carrier device 23 of the x-ray detector 21 is similarly assigned an x-ray detector drive device 31. The x-ray source drive device 30 and the x-ray detector drive device 31 are effectively connected to a control device 50. The x-ray source drive device 30 or the x-ray detector drive device 31 can be of any design.

On the one hand the control device 50 controls the recording of the projections, i.e. typically dose, recording rate, tube voltage etc., and on the other the x-ray source drive device 30 as well as the x-ray detector-drive device 31. In addition the control device 50 is supplied with the position and/or orientation of the x-ray source 20 and/or x-ray detector 20 for each projection recorded by means of the x-ray beams output by the x-ray source 20, which are needed for determining a spatial presentation of an object under examination. To this end a position recording system for recording the position and/or orientation of x-ray source 20 and/or position and/or orientation of x-ray detector 21 can be provided.

The control device 50 can also control the inclination of the x-ray source 20 relative to the x-ray source carrier device 22 and/or the inclination of the x-ray detector 21 relative to the x-ray detector carrier device 23. The control of the inclination, i.e. the orientation of x-ray source 20 and x-ray detector 21 is necessary for a movement of the x-ray source 20 or of the x-ray detector 21 on a non-self-contained trajectory in which the distance between x-ray source 20 or x-ray detector 21 and associated central axis A1 or A2 changes. Advantageously a central axis A1 lies essentially centered both for self-contained trajectories and also for non-self-contained trajectories. The adaptation of the orientation or the inclination of x-ray source 20 and x-ray detector 21, so that the central x-ray beams leaving the x-ray source 20 essentially always hit the central point of the detector surface presented by the x-ray detector 21, occurs as a rule by means of an x-ray source 20 movable relative to the x-ray source carrier device 22 and an x-ray detector movable relative to the x-ray detector carrier device 23.

With these types of movement, x-ray source 20 and also x-ray detector 21 are as a rule moved directly by means of an x-ray source drive device 30 or an x-ray detector drive device 31 relative to the x-ray source carrier device 22 or the x-ray detector carrier device 23 on a non-self-contained trajectory. This changes the distance between x-ray source 20 or x-ray detector 21 and the central axis A1 or A2. If the orientation of x-ray source 20 and x-ray detector 21 is not subsequently changed, the central x-ray beam $X_s$ no longer passes through the center of the area of examination $U_z$. To ensure, for this type of movement of x-ray source 20 and x-ray detector 21, that the central x-ray beam $X_s$ continues to pass through the center of the examination area $U_z$, adaptation of the inclination or orientation of x-ray source 20 and x-ray detector 21 for mutual alignment is required. This alignment of the orientations of x-ray source 20 and x-ray detector 21 is advantageously undertaken by means of the control device 50.

The spatial presentation is determined from the projection datasets and from the position and/or orientation data of x-ray source 20 and x-ray detector 21 by means of a data processing device 60. To this end reconstruction methods are used which allow two-dimensional projection datasets recorded by means of said x-ray apparatus 10 to be transferred to a spatial presentation. After the spatial presentation has been reconstructed, the spatial presentation determined is preferably output on an input/output device 70.

FIG. 1 shows, in addition to the x-ray apparatus 10, a patient support apparatus 40 on which an object under examination U is arranged. At the beginning of the examination the x-ray apparatus 10 and/or the patient support device 40 are positioned such that the central axis A1 or A2 essentially runs through a center of the examination area $U_z$ of the object under examination U.

In the exemplary embodiment the rigid attachment of x-ray source 20 and x-ray detector 21 to the associated x-ray source carrier device 22 or the x-ray detector carrier device 23 enables high speeds of rotation for the x-ray source carrier device 22 or x-ray detector carrier device 23 to be reached, enabling the examination time to be reduced. In such cases projection datasets will be recorded at an imaging rate adapted to the speed of rotation.

The imaging rate and speed of rotation of the x-ray source carrier device 22 or of the x-ray detector carrier device 23 are advantageously adapted so that a lowest possible dose load is produced on the object under examination U, the examination time is kept as short as possible and a sufficient number of two-dimensional projection datasets are recorded from different projection directions for determination of a spatial presentation.

FIG. 1 in this case also shows an x-ray source 20' and an x-ray detector 21' after a half rotation of the respective carrier device 22 or 23, with a central x-ray beam $X_s'$ also assigned to this position and orientation also being shown in the figure. In the exemplary embodiment the central x-ray beams $X_s$ or $X_s'$ of the plurality of recorded datasets thus describe an outer surface of a double sphere. Depending on the trajectory selected, the central x-ray beams $X_s$ or. $X_s'$ predetermined by the plurality of projection datasets can describe any symmetric, asymmetric, closed or open body.

Figure 2:
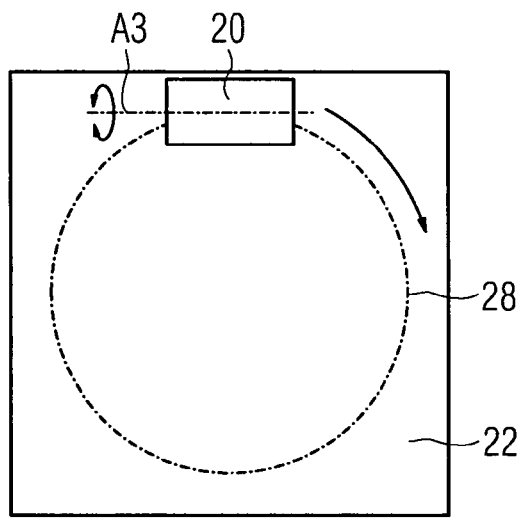
FIG. 2 is an overhead view of an x-ray source able to be moved on a circular trajectory relative to a rectangular carrier device.

FIG. 2 shows a rectangular x-ray source carrier device 22 with circular trajectory 28, marked on it on which an x-ray source 20 can be moved. The trajectory 28 is predetermined in the form of a guide rail for example. By means of an x-ray source drive device 30 not shown in FIG. 2, see FIG. 1, the x-ray source 20 can be moved along the trajectory 28. When this is done during an examination a plurality of projection datasets of an object under examination U not shown in FIG. 2 are recorded, see FIG. 1.

For non self-contained trajectories or central axes A1 lying essentially not centered relative to the trajectory—both arrangements not being shown in the figures—a rotation of the x-ray source 20 relative to the x-ray source carrier device 22 around a pivot axis A3 can be provided, to enable x-ray source 20 and x-ray detector 21, see FIG. 1, to be aligned to each other. In a similar fashion this can be provided for an x-ray detector 21.

Also conceivable is a combination of an x-ray source or x-ray detector connected rigidly to an associated carrier device, with an x-ray detector or x-ray source movable relative to the associated carrier device.

Figure 3:
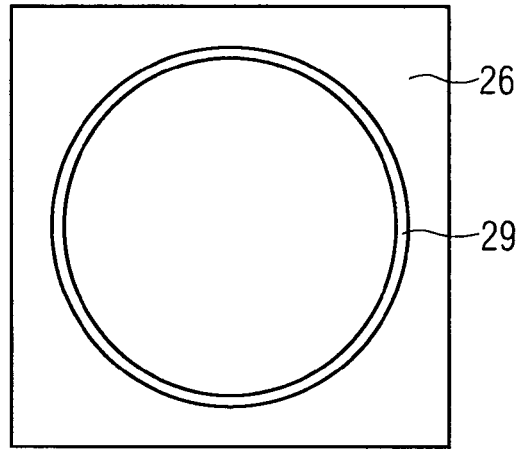
FIG. 3 is an overhead view of a housing of an x-ray device.

FIG. 3 shows a housing of an x-ray source device with a circular x-ray source exit slot 29. If necessary the slot width, regardless of the type of slot, should be able to be adjusted to obtain a desired beam restriction of the x-ray beams for the inventive x-ray apparatus.

Figure 4:
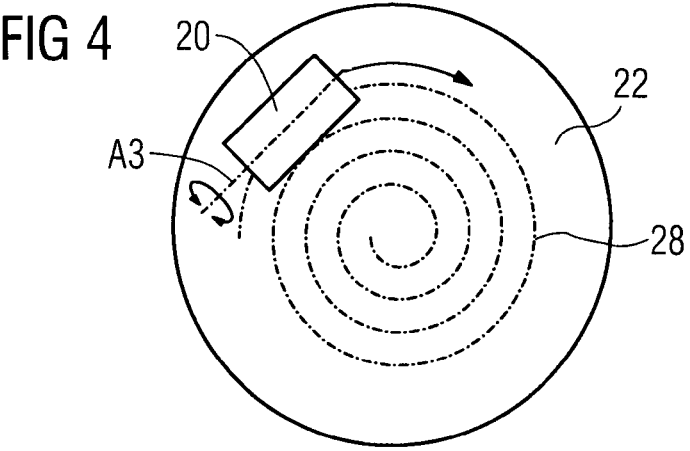
FIG. 4 is an overhead view of an x-ray source able to be moved on a helical trajectory relative to a circular carrier device.

FIG. 4 shows a circular x-ray source carrier device 22 with a helical trajectory 28, marked on it on which an x-ray source 20 can be moved.

The invention claimed is:

1. An x-ray apparatus, comprising:
    an x-ray source moved in a first characteristic trajectory adapted to an examination environment in a first plane that emits x-ray beams; and
    an x-ray detector moved in a second characteristic trajectory adapted to the examination environment in a second plane parallel to the first plane that detects the x-ray beams penetrating an object to record a plurality of two-dimensional projections of the object in a plurality of projection directions,
    wherein the x-ray source and the x-ray detector are configured to align to each other so that a central x-ray beam always hits a surface of the x-ray detector at a right angle.

2. The x-ray apparatus as claimed in claim 1, wherein the first plane and the second plane are not coincident.

3. The x-ray apparatus as claimed in claim 1, wherein the first plane and the second plane are arranged horizontally.

4. The x-ray apparatus as claimed in claim 1, wherein a movement of the x-ray detector is adapted to a movement of the x-ray source.

5. The x-ray apparatus as claimed in claim 4, wherein the movements of the x-ray source and the x-ray detector are self-contained movements.

6. The x-ray apparatus as claimed in claim 4, wherein the movements of the x-ray source and the x-ray detector comprise at least one turning point.

7. The x-ray apparatus as claimed in claim 1, wherein the x-ray source or the x-ray detector is arranged on a movable carrier device.

8. The x-ray apparatus as claimed in claim 7, wherein a position or an orientation of the movable carrier device is adjustable relative to the object.

9. The x-ray apparatus as claimed in claim 7, wherein the movable carrier device is arranged on a drive device.

10. The x-ray apparatus as claimed in claim 9, wherein the drive device is connected to a control device that controls the movement of the x-ray source or the x-ray detector.

11. The x-ray apparatus as claimed in claim 1, wherein the object is arranged between the first plane and the second plane.

12. The x-ray apparatus as claimed in claim 1, wherein the projection directions are obtained by moving the x-ray source and the x-ray detector adapted to the movement of the x-ray source.

13. The x-ray apparatus as claimed in claim 1, wherein a spatial presentation of the object is determined based on the two-dimensional projections of the object.

14. The x-ray apparatus as claimed in claim 1, wherein the first characteristic trajectory has a phase difference of 180 degrees with respect to the second characteristic trajectory.

15. The x-ray apparatus as claimed in claim 1, wherein the first characteristic trajectory is helical.

16. A method for operating an x-ray apparatus comprising an x-ray source and an x-ray detector, comprising:
moving the x-ray source in a first characteristic trajectory adapted to an examination environment in a first plane;
moving the x-ray detector in a second characteristic trajectory adapted to the examination environment in a second plane parallel to the first plane; and
operating the x-ray apparatus by adapting the movement of the x-ray detector to the movement of the x-ray source so that a central x-ray beam emitted from the x-ray source always hits a surface of the x-ray detector at a right angle.

17. The method as claimed in claim 16, wherein the first plane and the second plane are not coincident.

18. The method as claimed in claim 16, wherein the first plane and the second plane are arranged horizontally.

19. The method as claimed in claim 16, wherein the movements of the x-ray source and the x-ray detector are self-contained movements.

20. The method as claimed in claim 16, wherein the movements of the x-ray source and the x-ray detector comprise at least one turning point.

* * * * *